US009879281B2

(12) United States Patent
Son et al.

(10) Patent No.: US 9,879,281 B2
(45) Date of Patent: Jan. 30, 2018

(54) RECOMBINANT VACCINIA VIRUS DERIVED FROM KVAC103 STRAIN

(71) Applicant: Korea Centers for Disease Control and Prevention, Chungcheongbuk-do (KR)

(72) Inventors: Ho Sun Son, Daejeon (KR); Sang Gu Yeo, Seoul (KR); Sang Won Lee, Seoul (KR)

(73) Assignee: KOREA CENTERS FOR DISEASE CONTROL AND PREVENTION, Chungcheongbuk-Do (KR)

(*) Notice: Subject to any disclaimer, the term of this patent is extended or adjusted under 35 U.S.C. 154(b) by 41 days.

(21) Appl. No.: 14/883,752

(22) Filed: Oct. 15, 2015

(65) Prior Publication Data

US 2016/0108371 A1 Apr. 21, 2016

(30) Foreign Application Priority Data

Oct. 16, 2014 (KR) ........................ 10-2014-0140151

(51) Int. Cl.
*A61K 39/07* (2006.01)
*C12N 15/86* (2006.01)

(52) U.S. Cl.
CPC .............. *C12N 15/86* (2013.01); *A61K 39/07* (2013.01); *C12N 2710/24121* (2013.01); *C12N 2710/24134* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 8,741,308 | B2 | 6/2014 | Howley et al. |
| 9,012,214 | B2 | 4/2015 | Tangy et al. |
| 2012/0328650 | A1 | 12/2012 | Chaplin et al. |

FOREIGN PATENT DOCUMENTS

| | | | |
|---|---|---|---|
| KR | 20040108798 | A | 12/2004 |
| KR | 20050024359 | A | 3/2005 |

(Continued)

OTHER PUBLICATIONS

Son et al. "Development of a Recombinant Viral Vector Using the Highly Attenuated Korean Vaccinia Virus Strain, KVAC103", poster F034 presented at the International Meeting of the Federation of Korean Microbiological Societies Microbiology; from Basic Science to Applied Technology on Oct. 17 and 18, 2013 at the The-K Seoul Hotel, Seoul, Korea.*

(Continued)

*Primary Examiner* — Janet L Andres
*Assistant Examiner* — Stuart W Snyder
(74) *Attorney, Agent, or Firm* — RatnerPrestia

(57) ABSTRACT

Disclosed herein is a novel recombinant virus vector derived from the attenuated vaccinia virus strain KVAC103. The recombinant virus vector is obtained by inserting an exogenous gene into the KVAC103 and may be used as a safe vaccine delivery vehicle in mammals. Particularly, recombinant viruses obtained by rescuing some of the genes deleted from the parent virus have an enhanced ability to proliferate in cells being cultured, and thus are easily produced. In addition, the recombinant viruses express an increased level of an exogenous antigen, and thus has enhanced immunogenic efficacy. Such recombinant virus vectors may be used in vaccines for preventing diseases, therapeutic vaccines, and molecular biological studies.

7 Claims, 13 Drawing Sheets
(10 of 13 Drawing Sheet(s) Filed in Color)

(56) References Cited

FOREIGN PATENT DOCUMENTS

| | | | |
|---|---|---|---|
| KR | 20080032016 | A | 4/2008 |
| WO | WO 2010/031837 | A1 | 3/2010 |

OTHER PUBLICATIONS

Stickl et al. "MVA-Stage Vaccination Against Smallpox,".Dtsch Med Wochenschr 1974; 99(47): 2386-2392. Abstract.
Hendrickson et al., "Orthopoxvirus Genome Evolution: The Role of Gene Loss," Viruses 2010, 2, 1933-1967.
Rosel et al., "Conserved TAAATG Sequence at the Transcriptional and Translational Initiation Sites of Vaccinia Virus Late Genes Deduced by Structural and Functional Analysis of the HindIII H Genome Fragment," Journal of Virology, vol. 60, No. 2, Nov. 1986, 436-449.
Yuen et al., "Early promoter-binding factor from vaccinia virions," Proc. Natl. Acad. Sci. USA, vol. 84, Sep. 1987, 6069-6073.
Davison et al., "Structure of Vaccinia Virus Late Promoters," J. Mol. Biol. (1989) 210, 771-784.
Davison et al., "Structure of Vaccinia Virus Early Promoters," J. Mal. Biol. (1989) 210, 749-769.
Chakrabarti et al., "Compact, Synthetic, Vaccinia Virus Early/Late Promoter for Protein Expression," BioTechniques 23. Dec. 1997, 1084-1097.

* cited by examiner

【Figure 1】

```
        ClaI                                                     BamHI
  1   ATCGATTAAAAATTGAAATTTTATTTTTTTTTTTTGGAATATAAATAAGGATCCTAGGCC
                 synthetic early-to-late promoter

        SfiI     RsrII    ApaI AsiSI
 61   ACCATGGCCGGACCGGGCCCAGCGATCGCAATGGTGAGCAAGGGCGAGGAGCTGTTCACC
  1      M  A  G  P  G  P  A  I  A  M  V  S  K  G  E  E  L  F  T

121   GGGGTGGTGCCCATCCTGGTCGAGCTGGACGGCGACGTAAACGGCCACAAGTTCAGCGTG
 20   G  V  V  P  I  L  V  E  L  D  G  D  V  N  G  H  K  F  S  V

181   TCCGGCGAGGGCGAGGGCGATGCCACCTACGGCAAGCTGACCCTGAAGTTCATCTGCACC
 40   S  G  E  G  E  G  D  A  T  Y  G  K  L  T  L  K  F  I  C  T

241   ACCGGCAAGCTGCCCGTGCCCTGGCCCACCCTCGTGACCACCCTGACCTACGGCGTGCAG
 60   T  G  K  L  P  V  P  W  P  T  L  V  T  T  L  T  Y  G  V  Q

301   TGCTTCAGCCGCTACCCCGACCACATGAAGCAGCACGACTTCTTCAAGTCCGCCATGCCC
 80   C  F  S  R  Y  P  D  H  M  K  Q  H  D  F  F  K  S  A  M  P

361   GAAGGCTACGTCCAGGAGCGCACCATCTTCTTCAAGGACGACGGCAACTACAAGACCCGC
100   E  G  Y  V  Q  E  R  T  I  F  F  K  D  D  G  N  Y  K  T  R

421   GCCGAGGTGAAGTTCGAGGGCGACACCCTGGTGAACCGCATCGAGCTGAAGGGCATCGAC
120   A  E  V  K  F  E  G  D  T  L  V  N  R  I  E  L  K  G  I  D

481   TTCAAGGAGGACGGCAACATCCTGGGGCACAAGCTGGAGTACAACTACAACAGCCACAAC
140   F  K  E  D  G  N  I  L  G  H  K  L  E  Y  N  Y  N  S  H  N

541   GTCTATATCATGGCCGACAAGCAGAAGAACGGCATCAAGGTGAACTTCAAGATCCGCCAC
160   V  Y  I  M  A  D  K  Q  K  N  G  I  K  V  N  F  K  I  R  H

601   AACATCGAGGACGGCAGCGTGCAGCTCGCCGACCACTACCAGCAGAACACCCCCATCGGC
180   N  I  E  D  G  S  V  Q  L  A  D  H  Y  Q  Q  N  T  P  I  G

661   GACGGCCCCGTGCTGCTGCCCGACAACCACTACCTGAGCACCCAGTCCGCCCTGAGCAAA
200   D  G  P  V  L  L  P  D  N  H  Y  L  S  T  Q  S  A  L  S  K

721   GACCCCAACGAGAAGCGCGATCACATGGTCCTGCTGGAGTTCGTGACCGCCGCCGGGATC
220   D  P  N  E  K  R  D  H  M  V  L  L  E  F  V  T  A  A  G  I

                                            AsiSI RsrII ApaI  SfiI   XhoI
781   ACTCTCGGCATGGACGAGCTGTACAAGTAAGCGATCGCGGTCCGGGCCCTGCAGGCCCTC
240   T  L  G  M  D  E  L  Y  K  *  248

           PacI EcoRI
841   GAGTTAATTAAGAATTC
```

【Figure 2】
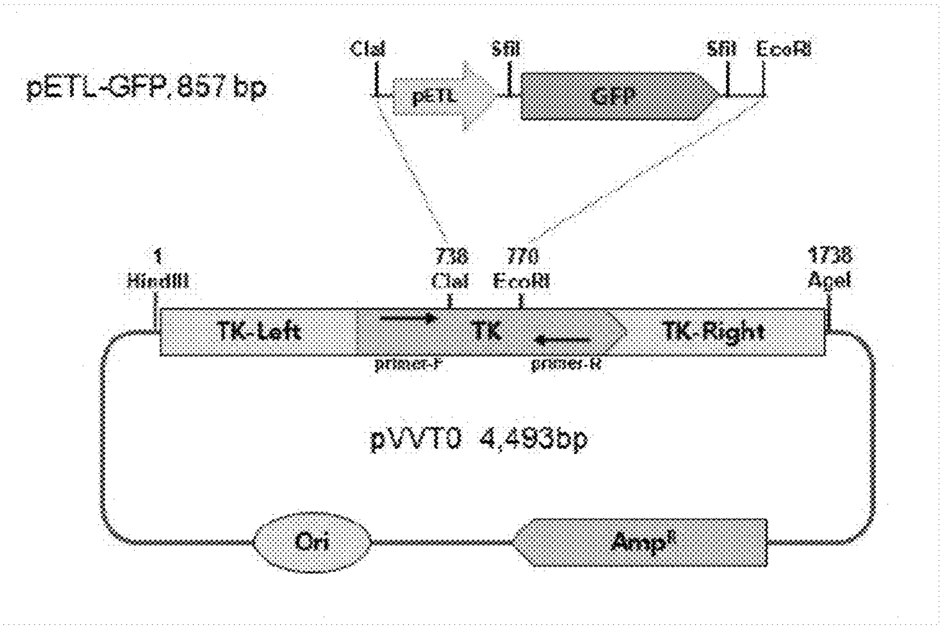
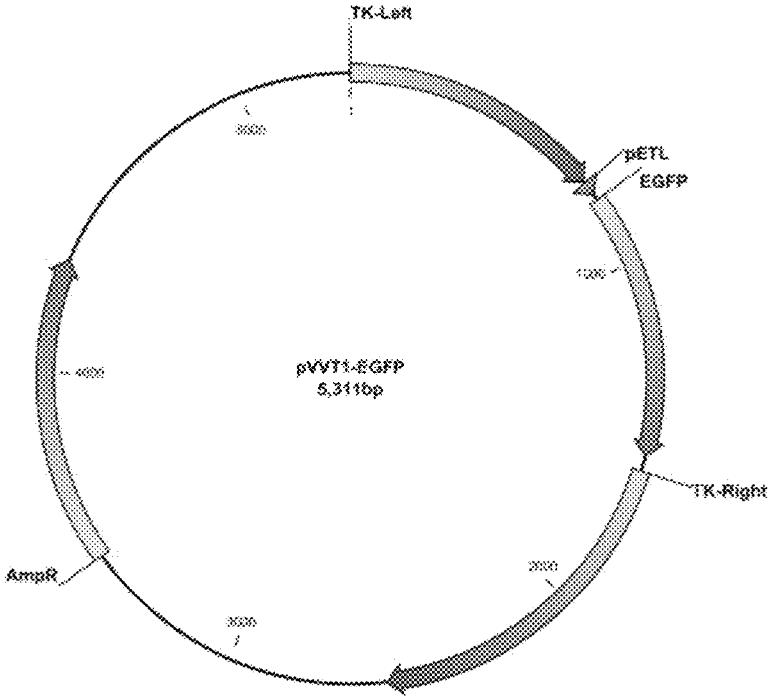

【Figure 3】
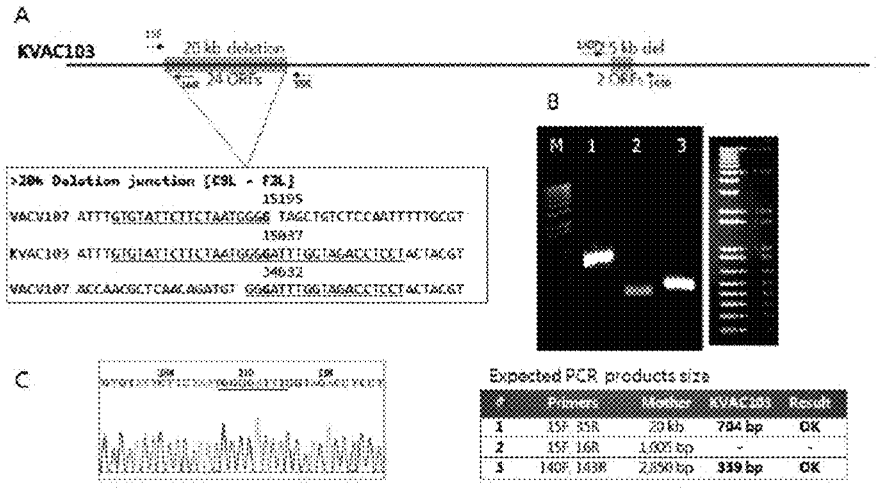

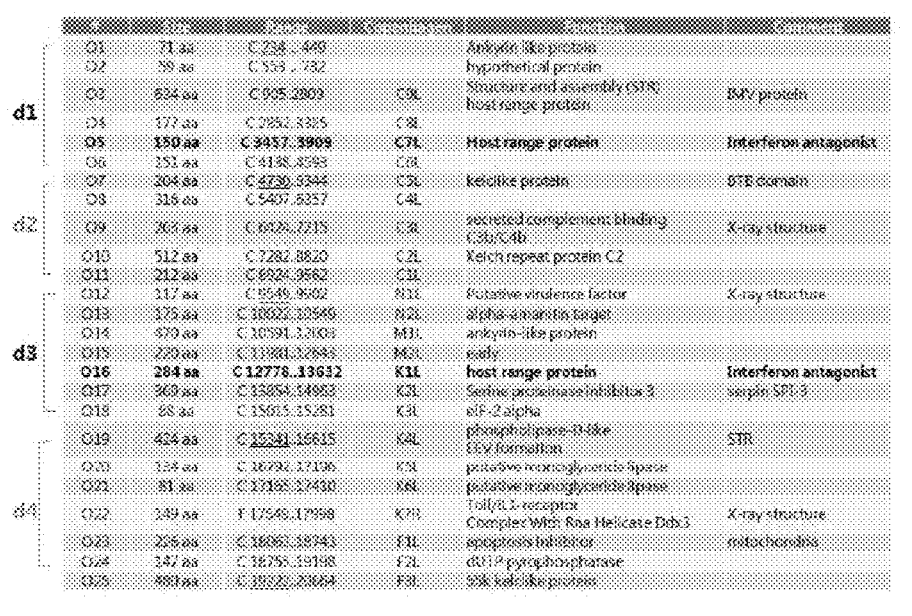

【Figure 4】

| | | | | | | |
|---|---|---|---|---|---|---|
| | O1 | 71 aa | C 238..449 | | Ankyrin-like protein | |
| | O2 | 59 aa | C 535..732 | | hypothetical protein | |
| | O3 | 834 aa | C 905..2809 | C9L | Structure and assembly (STR) host range protein | IMV protein |
| d1 | O4 | 177 aa | C 2852..3325 | C8L | | |
| | **O5** | **150 aa** | **C 3457..3909** | **C7L** | **Host range protein** | **Interferon antagonist** |
| | O6 | 151 aa | C 4138..4593 | C6L | | |
| | O7 | 204 aa | C 4730..5344 | C5L | Kelchlike protein | BTB domain |
| | O8 | 318 aa | C 5407..6357 | C4L | | |
| d2 | O9 | 263 aa | C 6028..7215 | C3L | secreted complement binding C3b/C4b | X-ray structure |
| | O10 | 512 aa | C 7282..8820 | C2L | Kelch repeat protein C2 | |
| | O11 | 212 aa | C 8924..9562 | C1L | | |
| | O12 | 117 aa | C 9549..9902 | N1L | Putative virulence factor | X-ray structure |
| | O13 | 175 aa | C 10022..10549 | N2L | alpha-amanitin target | |
| | O14 | 470 aa | C 10591..12003 | M1L | ankyrin-like protein | |
| d3 | O15 | 220 aa | C 11981..12643 | M2L | early | |
| | **O16** | **284 aa** | **C 12778..13632** | **K1L** | **host range protein** | **Interferon antagonist** |
| | O17 | 369 aa | C 13854..14963 | K2L | Serine proteinase inhibitor 3 | serpin SPI-3 |
| | O18 | 88 aa | C 15015..15281 | K3L | eIF-2 alpha | |
| | O19 | 424 aa | C 15341..16615 | K4L | phospholipase-D-like EEV formation | STR |
| | O20 | 134 aa | C 16732..17136 | K5L | putative monoglyceride lipase | |
| | O21 | 81 aa | C 17185..17430 | K6L | putative monoglyceride lipase | |
| d4 | O22 | 149 aa | F 17549..17998 | K7R | Toll/IL1-receptor Complex With Rna Helicase Ddx3 | X-ray structure |
| | O23 | 226 aa | C 18063..18743 | F1L | apoptosis inhibitor | mitochondria |
| | O24 | 147 aa | C 18755..19198 | F2L | dUTP pyrophosphatase | |
| | O25 | 481 aa | C 19522..20964 | F3L | 55k kelchlike protein | |

【Figure 5】
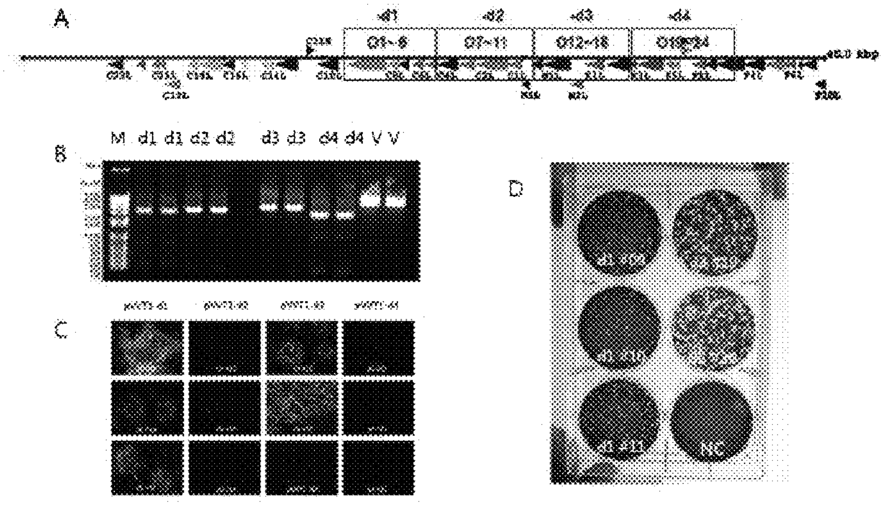

【Figure 6】
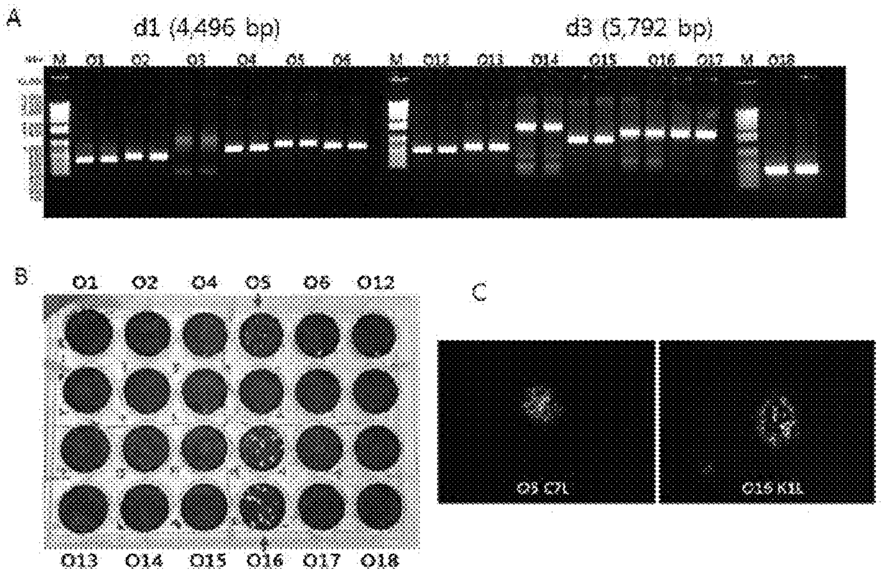

【Figure 7】

```
LOCUS       ORF5(C7L)       714 bp    DNA     linear   2012-11-13
DEFINITION
FEATURES             Location/Qualifiers
     Protein_Feature 256..708
                     /translation=C7L
ORIGIN
        1 CTCGAGCGTG ATGATGTAGA TAGATAATTT TTTTTCCTAA ACTGATTTCT CTGTTTAAAT
       61 TCGTAGCGAT ATATATAAAA CAACATGTAA TTAATTAATA AACTTTAAGA CATGTGTGGT
      121 ATACTAAGAT GGTTGGCTTA TTCCATAGTA GCTTGTGGAA TTTATAAACT TATGATAGTA
      181 AAACTAGTAC CCAATATGTA AAGATGAAAA AGTAAATTAC TATTAACGCC GTCGGTATTC
      241 GTTCATCCAT TCAGTATGGG TATACAGCAC GAATTCGACA TCATTATTAA TGGAGATATC
      301 GCGTTGAGAA ATTTACAGTT ACATAAAGGG GATAACTACG GATGCAAACT AAAAATTATT
      361 TCGAATGATT ACAAGAAATT AAAGTTTAGA TTCATTATAC GCCCAGATTG GTCGGAAATC
      421 GACGAGGTCA AAGGATTAAC CGTATTTGCA AACAACTATG CGGTGAAAGT TAATAAGGTA
      481 GATGACACGT TCTATTACGT AATATATGAG GCTGTAATAC ATCTGTATAA CAAAAAAACA
      541 GAGATATTGA TTTATTCTGA TGATGAGAAC GAGCTCTTCA AACACTATTA CCCATACATC
      601 AGTCTAAATA TGATTAGTAA AAAGTATAAA GTTAAAGAAG AGAACTACTC ATCCCCGTAT
      661 ATAGAACATC CGTTAATCCC GTATAGAGAT TATGAGTCCA TGGATTAA CTCGAG
//

>ORF5(C7L) 150aa
MGIQHEFDII INGDIALRNL QLHKGDNYGC KLKIISNDYK KLKFRFIIRP DWSEIDEVKG
LTVFANNYAV KVNKVDDTFY YVIYEAVIHL YNKKTEILIY SDDENELFKH YYPYISLNMI
SKKYKVKEEN YSSPYIEHPL IPYRDYESMD *
```

【Figure 8】

```
LOCUS       ORF16(K1L)      1100 bp    DNA     linear   2012-11-13
DEFINITION
FEATURES             Location/Qualifiers
     Protein_Feature 240..1094
                     /label=K1L
ORIGIN
        1 CTCGAGGAAT CTCCTTAATA TGGGTACGGT GTAAGGAATC ATTATTTTAT TTATATTGAT
       61 GGGTACGTGA AATCTGAATT TTCTTAATAA ATATTATTTT TATTAAATGT GTATATGTTG
      121 TTTTGCGATA GCCATGTATC TACTAATCAG ATCTATTAGA GATATTATTA ATTCTGGTGC
      181 AATATGACAA AATTATAAAA AATGAAAAAA TATACACTAA TTAGCGTCTC GTTTCAGACA
      241 TGGATCTGTC ACGAATTAAT ACTTGGAAGT CTAAGCAGCT GAAAAGCTTT CTCTCTAGTA
      301 AAGATACATT TAAGGCGGAT GTCCATGGAC ATAGTGCCTT GTATTATGCA ATAGCTGATA
      361 ATAACGTGCG TCTAGTATGT ACGTTGTTGA ACGCTGGAGC ATTGAAAAAT CTTCTAGAGA
      421 ATGAATTTCC ATTACATCAG GCAGCCACAT TGGAAGATAC CAAAATAGTA AAGATTTTGC
      481 TATTCAGTGG ACTGGATGAT TCACAATTTG ATGACAAGGG AAACACTGCA TTGTATTATG
      541 CGGTTGATAG TGGTAACATG CAAACGGTAA AACTGTTTGT TAAGAAAAAT TGGAGACTGA
      601 TGTTCTATGG GAAAACTGGA TGGAAAACTT CATTTTATCA TGCCGTCATG CTTAATGATG
      661 TAAGTATTGT TTCCTACTTT CTTTCAGAGA TACCATCTAC TTTTGATCTG GCTATTCTCC
      721 TTAGTTGTAT TCACATCACT ATAAAAAATG GACACGTGGA TATGATGATT CTCTTGCTCG
      781 ACTATATGAC GTCGACAAAC ACCAATAATT CCCTTCTCTT CATTCCGGAC ATTAAATTGG
      841 CTATAGATAA TAAAGACATT GAGATGTTAC AGGCTCTGTT CAAATACGAC ATTAATATCT
      901 ATTCTGCTAA TCTGGAAAAT GTACTATTGG ATGATGCCGA AATAGCTAAA ATGATTATAG
      961 AAAAGCATGT TGAATACAAG TCTAACTCCT ATACAAAAGA TCTCGATATC GTCAAGAATA
     1021 ATAAATTGGA TGAAATAATT AGCAAAAACA AGGAACTCAG ACTCATGTAC GTCAATTGTG
     1081 TAAAGAAAAA CTAA CTCGAG
//
>ORF16(K1L) 285 aa
        1 MDLSRINTWK SKQLKSFLSS KDTFKADVHG HSALYYAIAD NNVRLVCTLL NAGALKNLLE
       61 NEFPLHQAAT LEDTKIVKIL LFSGLDDSQF DDKGNTALYY AVDSGNMQTV KLFVKKNWRL
      121 MFYGKTGWKT SFYHAVMLND VSIVSYFLSE IPSTFDLAIL LSCIHITIKN GHVDMMILLL
      181 DYMTSTNTNN SLLFIPDIKL AIDNKDIEML QALFKYDINI YSANLENVLL DDAEIAKMII
      241 EKHVEYKSNS YTKDLDIVKN NKLDEIISKN KELRLMYVNC VKKN*
//
```

【Figure 9】
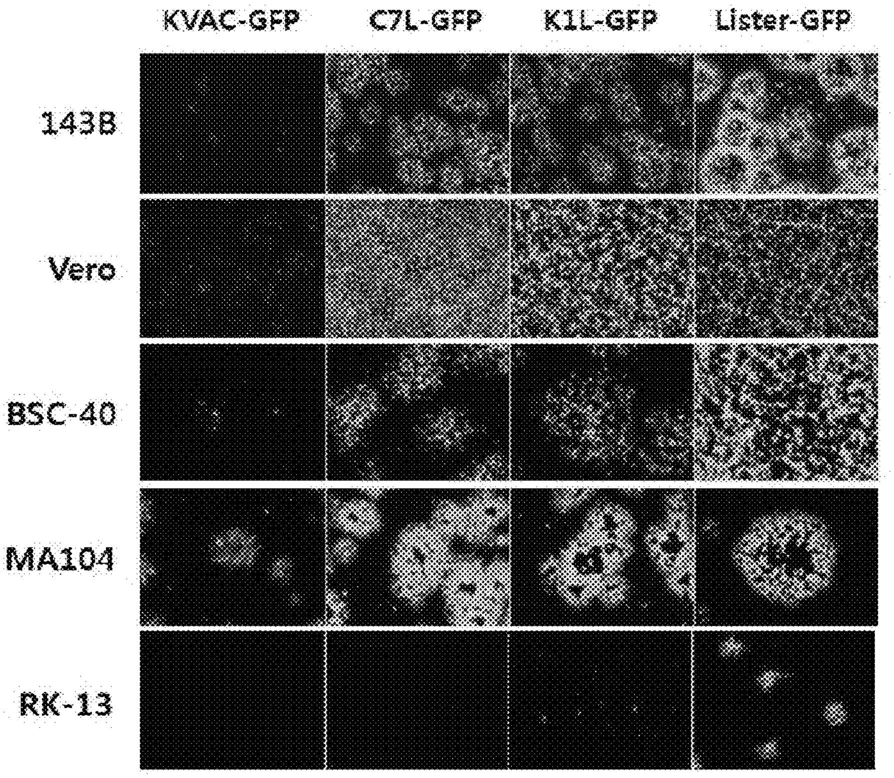

【Figure 10】
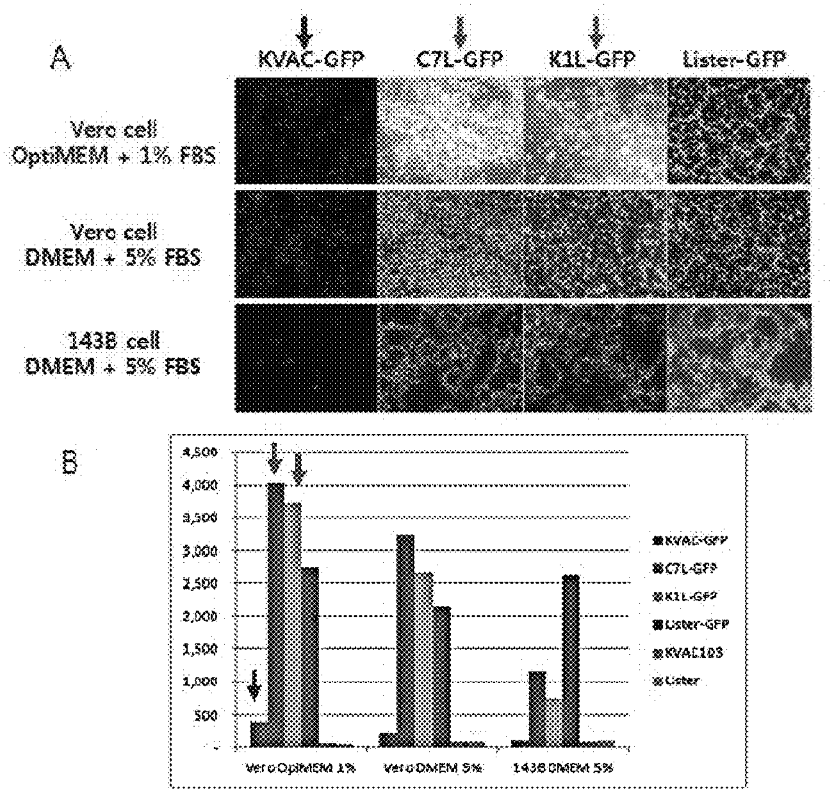

【Figure 11】
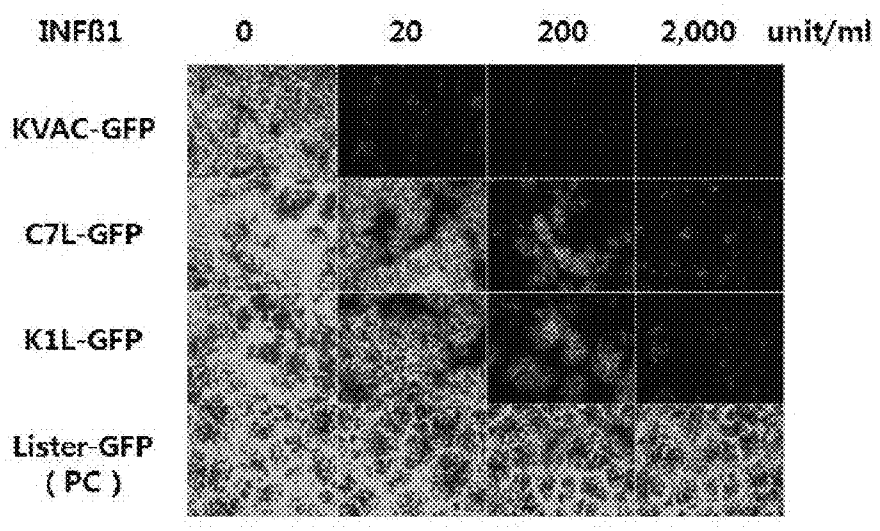

【Figure 12】
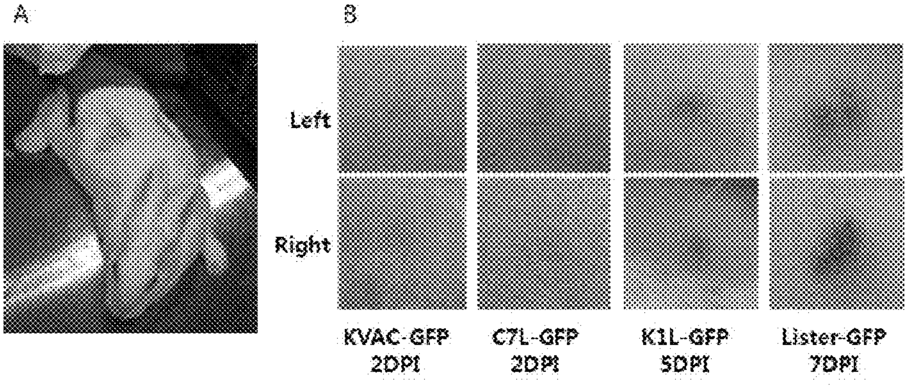

【Figure 13】
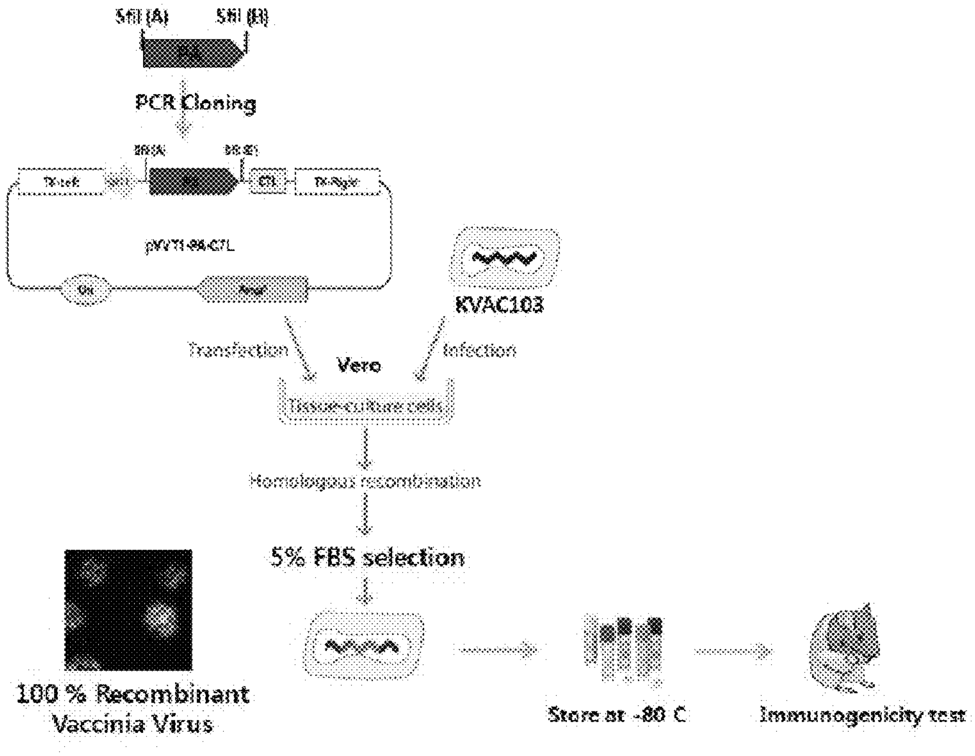

SEQUENCE LISTING

```
<160> NUMBER OF SEQ ID NOS: 43

<210> SEQ ID NO 1
<211> LENGTH: 5311
<212> TYPE: DNA
<213> ORGANISM: Artificial Sequence
<220> FEATURE:
<223> OTHER INFORMATION: Synthetic

<400> SEQUENCE: 1

agcttttgcg atcaataaat ggatcacaac cagtatctct taacgatgtt cttcgcagat      60

gatgattcat tttttaagta tttggctagt caagatgatg aatcttcatt atctgatata     120

ttgcaaatca ctcaatatct agactttctg ttattattat tgatccaatc aaaaaaataa     180

ttagaagccg tgggtcattg ttatgaatct ctttcagagg aatacagaca attgacaaaa     240

ttcacagact ctcaagattt taaaaaactg tttaacaagg tccctattgt tacagatgga     300

agggtcaaac ttaataaagg atatttgttc gactttgtga ttagtttgat gcgattcaaa     360

aaagaatcct ctctagctac caccgcaata gatcctatta gatacataga tcctcgtcgt     420

gatatcgcat tttctaacgt gatggatata ttaaagtcga ataaagtgaa caataattaa     480

ttctttattg tcatcatgaa cggcggacat attcagttga taatcggccc catgttttca     540

ggtaaaagta cagaattaat tagacgagtt agacgttatc aaatagctca atataaatgc     600

gtgactataa aatattctaa cgataataga tacggaacgg gactatggac gcatgataag     660

aataattttg aagcattgga agcaactaaa ctatgcgatg tcttggaatc aattacagat     720

ttctccgtga taggtatcga ttaaaaattg aaattttatt ttttttttt ggaatataaa     780

taaggatcct aggccaccat ggccggaccg ggcccagcga tcgcaatggt gagcaagggc     840
```

-continued

```
gaggagctgt tcaccggggt ggtgcccatc ctggtcgagc tggacggcga cgtaaacggc    900
cacaagttca gcgtgtccgg cgagggcgag ggcgatgcca cctacggcaa gctgaccctg    960
aagttcatct gcaccaccgg caagctgccc gtgccctggc ccaccctcgt gaccaccctg   1020
acctacggcg tgcagtgctt cagccgctac cccgaccaca tgaagcagca cgacttcttc   1080
aagtccgcca tgcccgaagg ctacgtccag gagcgcacca tcttcttcaa ggacgacggc   1140
aactacaaga cccgcgccga ggtgaagttc gagggcgaca ccctggtgaa ccgcatcgag   1200
ctgaagggca tcgacttcaa ggaggacggc aacatcctgg ggcacaagct ggagtacaac   1260
tacaacagcc acaacgtcta tatcatggcc gacaagcaga agaacggcat caaggtgaac   1320
ttcaagatcc gccacaacat cgaggacggc agcgtgcagc tcgccgacca ctaccagcag   1380
aacaccccca tcggcgacgg ccccgtgctg ctgcccgaca accactacct gagcacccag   1440
tccgccctga gcaaagaccc caacgagaag cgcgatcaca tggtcctgct ggagttcgtg   1500
accgccgccg ggatcactct cggcatggac gagctgtaca agtaagcgat cgcggtccgg   1560
gccctgcagg ccctcgagtt aattaagaat tctgtgagcg tatggcaaac gaaggaaaaa   1620
tagttatagt agccgcactc gatgggacat ttcaacgtaa accgtttaat aatattttga   1680
atcttattcc attatctgaa atggtggtaa aactaactgc tgtgtgtatg aaatgcttta   1740
aggaggcttc cttttctaaa cgattgggtg aggaaaccga gatagaaata ataggaggta   1800
atgatatgta tcaatcggtg tgtagaaagt gttacatcga ctcataatat tatatttttt   1860
atctaaaaaa ctaaaaataa acattgatta aattttaata taatacttaa aaatggatgt   1920
tgtgtcgtta gataaaccgt ttatgtattt tgaggaaatt gataatgagt tagattacga   1980
accagaaagt gcaaatgagg tcgcaaaaaa actaccgtat caaggacagt taaaactatt   2040
actaggagaa ttattttttc ttagtaagtt acagcgacac ggtatattag atggtgccac   2100
cgtagtgtat ataggatcgg ctcctggtac acatatacgt tatttgagag atcatttcta   2160
taatttagga gtgatcatca aatggatgct aattgacggc cgccatcatg atcctattct   2220
aaatggattg cgtgatgtga ctctagtgac tcggttcgtt gatgaggaat atctacgatc   2280
catcaaaaaa caactgcatc cttctaagat tattttaatt tctgatgtga gatccaaacg   2340
aggaggaaat gaacctagta cggcggattt actaagtaat tacgctctac aaaatgtcat   2400
gattagtatt ttaaaccccg tggcgtctag tcttaaatgg agatgcccgt ttccagatca   2460
atggatcaag gacttttata tcccacacgg taataaaatg ttacaacctt ttgctccttc   2520
atattcagct gaaatgagat tattaagtat ttataccggt attttctcct tacgcatctg   2580
tgcggtattt cacaccgcat acgtcaaagc aaccatagta cgcgccctgt agcggcgcat   2640
taagcgcggc gggtgtggtg gttacgcgca gcgtgaccgc tacacttgcc agcgccctag   2700
cgcccgctcc tttcgctttc ttcccttcct ttctcgccac gttcgccggc tttccccgtc   2760
aagctctaaa tcgggggctc cctttagggt tccgatttag tgctttacgg cacctcgacc   2820
ccaaaaaact tgatttgggt gatggttcac gtagtgggcc atcgccctga tagacggttt   2880
ttcgcccttt gacgttggag tccacgttct ttaatagtgg actcttgttc caaactggaa   2940
caacactcaa ccctatctcg ggctattctt ttgatttata agggattttg ccgatttcgg   3000
cctattggtt aaaaaatgag ctgatttaac aaaaatttaa cgcgaatttt aacaaaatat   3060
taacgtttac aattttatgg tgcactctca gtacaatctg ctctgatgcc gcatagttaa   3120
gccagccccg acacccgcca acacccgctg acgcgccctg acgggcttgt ctgctcccgg   3180
```

```
catccgctta cagacaagct gtgaccgtct ccgggagctg catgtgtcag aggttttcac   3240
cgtcatcacc gaaacgcgcg agacgaaagg gcctcgtgat acgcctattt ttataggtta   3300
atgtcatgat aataatggtt tcttagacgt caggtggcac ttttcgggga aatgtgcgcg   3360
gaacccctat ttgtttattt ttctaaatac attcaaatat gtatccgctc atgagacaat   3420
aaccctgata aatgcttcaa taatattgaa aaaggaagag tatgagtatt caacatttcc   3480
gtgtcgccct tattcccttt tttgcggcat tttgccttcc tgtttttgct cacccagaaa   3540
cgctggtgaa agtaaaagat gctgaagatc agttgggtgc acgagtgggt tacatcgaac   3600
tggatctcaa cagcggtaag atccttgaga gttttcgccc cgaagaacgt tttccaatga   3660
tgagcacttt taaagttctg ctatgtggcg cggtattatc ccgtattgac gccgggcaag   3720
agcaactcgg tcgccgcata cactattctc agaatgactt ggttgagtac tcaccagtca   3780
cagaaaagca tcttacggat ggcatgacag taagagaatt atgcagtgct gccataacca   3840
tgagtgataa cactgcggcc aacttacttc tgacaacgat cggaggaccg aaggagctaa   3900
ccgctttttt gcacaacatg ggggatcatg taactcgcct tgatcgttgg gaaccggagc   3960
tgaatgaagc cataccaaac gacgagcgtg acaccacgat gcctgtagca atggcaacaa   4020
cgttgcgcaa actattaact ggcgaactac ttactctagc ttcccggcaa caattaatag   4080
actggatgga ggcggataaa gttgcaggac cacttctgcg ctcggccctt ccggctggct   4140
ggtttattgc tgataaatct ggagccggtg agcgtgggtc tcgcggtatc attgcagcac   4200
tggggccaga tggtaagccc tcccgtatcg tagttatcta cacgacgggg agtcaggcaa   4260
ctatggatga acgaaataga cagatcgctg agataggtgc ctcactgatt aagcattggt   4320
aactgtcaga ccaagtttac tcatatatac tttagattga tttaaaactt catttttaat   4380
ttaaaaggat ctaggtgaag atcctttttg ataatctcat gaccaaaatc ccttaacgtg   4440
agttttcgtt ccactgagcg tcagaccccg tagaaaagat caaaggatct tcttgagatc   4500
cttttttct gcgcgtaatc tgctgcttgc aaacaaaaaa accaccgcta ccagcggtgg   4560
tttgtttgcc ggatcaagag ctaccaactc tttttccgaa ggtaactggc ttcagcagag   4620
cgcagatacc aaatactgtt cttctagtgt agccgtagtt aggccaccac ttcaagaact   4680
ctgtagcacc gcctacatac ctcgctctgc taatcctgtt accagtggct gctgccagtg   4740
gcgataagtc gtgtcttacc gggttggact caagacgata gttaccggat aaggcgcagc   4800
ggtcgggctg aacggggggt tcgtgcacac agcccagctt ggagcgaacg acctacaccg   4860
aactgagata cctacagcgt gagctatgag aaagcgccac gcttcccgaa gggagaaagg   4920
cggacaggta tccggtaagc ggcagggtcg gaacaggaga gcgcacgagg gagcttccag   4980
ggggaaacgc ctggtatctt tatagtcctg tcgggtttcg ccacctctga cttgagcgtc   5040
gatttttgtg atgctcgtca ggggggcgga gcctatggaa aaacgccagc aacgcggcct   5100
ttttacggtt cctggccttt tgctggcctt ttgctcacat gttctttcct gcgttatccc   5160
ctgattctgt ggataaccgt attaccgcct ttgagtgagc tgataccgct cgccgcagcc   5220
gaacgaccga gcgcagcgag tcagtgagcg aggaagcgga agagcgccca atacgcaaac   5280
cgcctctccc cgcgcgttgg ccgattcatt a                                  5311
```

<210> SEQ ID NO 2
<211> LENGTH: 714
<212> TYPE: DNA
<213> ORGANISM: Vaccinia virus

<400> SEQUENCE: 2

-continued ctcgagcgtg atgatgtaga tagataattt tttttcctaa actgatttct ctgtttaaat 60
tcgtagcgat atatataaaa caacatgtaa ttaattaata aactttaaga catgtgtggt 120
atactaagat ggttggctta ttccatagta gcttgtggaa tttataaact tatgatagta 180
aaactagtac ccaatatgta aagatgaaaa agtaaattac tattaacgcc gtcggtattc 240
gttcatccat tcagtatggg tatacagcac gaattcgaca tcattattaa tggagatatc 300
gcgttgagaa atttacagtt acataaaggg gataactacg gatgcaaact aaaaattatt 360
tcgaatgatt acaagaaatt aaagtttaga ttcattatac gcccagattg gtcggaaatc 420
gacgaggtca aaggattaac cgtatttgca aacaactatg cggtgaaagt taataaggta 480
gatgacacgt tctattacgt aatatatgag gctgtaatac atctgtataa caaaaaaaca 540
gagatattga tttattctga tgatgagaac gagctcttca aacactatta cccatacatc 600
agtctaaata tgattagtaa aaagtataaa gttaaagaag agaactactc atccccgtat 660
atagaacatc cgttaatccc gtatagagat tatgagtcca tggattaact cgag 714

<210> SEQ ID NO 3
<211> LENGTH: 1100
<212> TYPE: DNA
<213> ORGANISM: Vaccinia virus

<400> SEQUENCE: 3
ctcgaggaat ctccttaata tgggtacggt gtaaggaatc attattttat ttatattgat 60
gggtacgtga aatctgaatt ttcttaataa atattatttt tattaaatgt gtatatgttg 120
ttttgcgata gccatgtatc tactaatcag atctattaga gatattatta attctggtgc 180
aatatgacaa aattataaaa aatgaaaaaa tatacactaa ttagcgtctc gtttcagaca 240
tggatctgtc acgaattaat acttggaagt ctaagcagct gaaaagcttt ctctctagta 300
aagatacatt taaggcggat gtccatggac atagtgcctt gtattatgca atagctgata 360
ataacgtgcg tctagtatgt acgttgttga acgctggagc attgaaaaat cttctagaga 420
atgaatttcc attacatcag gcagccacat tggaagatac caaaatagta aagattttgc 480
tattcagtgg actggatgat tcacaatttg atgacaaggg aaacactgca ttgtattatg 540
cggttgatag tggtaacatg caaacggtaa aactgtttgt taagaaaaat tggagactga 600
tgttctatgg gaaaactgga tggaaaactt cattttatca tgccgtcatg cttaatgatg 660
taagtattgt ttcctacttt ctttcagaga taccatctac ttttgatctg gctattctcc 720
ttagttgtat tcacatcact ataaaaaatg gacacgtgga tatgatgatt ctcttgctcg 780
actatatgac gtcgacaaac accaataatt cccttctctt cattccggac attaaattgg 840
ctatagataa taaagacatt gagatgttac aggctctgtt caaatacgac attaatatct 900
attctgctaa tctggaaaat gtactattgg atgatgccga aatagctaaa atgattatag 960
aaaagcatgt tgaatacaag tctaactcct atacaaaaga tctcgatatc gtcaagaata 1020
ataaattgga tgaaataatt agcaaaaaca aggaactcag actcatgtac gtcaattgtg 1080
taaagaaaaa ctaactcgag 1100

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
gccgattcat taagcttttg cgatcaataa atgga 35

<210> SEQ ID NO 5
<211> LENGTH: 34
<212> TYPE: DNA
<213> ORGANISM: Artificial Sequence
<220> FEATURE:
<223> OTHER INFORMATION: Synthetic

<400> SEQUENCE: 5
ggagaaaata ccggtataaa tacttaataa tctc 34

<210> SEQ ID NO 6
<211> LENGTH: 34
<212> TYPE: DNA
<213> ORGANISM: Artificial Sequence
<220> FEATURE:
<223> OTHER INFORMATION: Synthetic

<400> SEQUENCE: 6
agtatttata ccggtatttt ctccttacgc atct 34

<210> SEQ ID NO 7
<211> LENGTH: 34
<212> TYPE: DNA
<213> ORGANISM: Artificial Sequence
<220> FEATURE:
<223> OTHER INFORMATION: Synthetic

<400> SEQUENCE: 7
tattgatcgc aaaagcttaa tgaatcggcc aacg 34

<210> SEQ ID NO 8
<211> LENGTH: 42
<212> TYPE: DNA
<213> ORGANISM: Artificial Sequence
<220> FEATURE:
<223> OTHER INFORMATION: Synthetic

<400> SEQUENCE: 8
taaaaattga aattttattt tttttttttg gaatataaat aa 42

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
aggaacagga tcattgtcat taca 24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
tgaactaaat gttccagatg agga 24

<210> SEQ ID NO 11
<211> LENGTH: 24

<212> TYPE: DNA
<213> ORGANISM: Artificial Sequence
<220> FEATURE:
<223> OTHER INFORMATION: Synthetic

<400> SEQUENCE: 11
agttctgcat tcaattcggt gagt 24

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
aattgtacca acggttcaag atgt 24

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
tcgtttatca acactaccgt taga 24

<210> SEQ ID NO 14
<211> LENGTH: 42
<212> TYPE: DNA
<213> ORGANISM: Artificial Sequence
<220> FEATURE:
<223> OTHER INFORMATION: Synthetic

<400> SEQUENCE: 14
agaattctta attaactcga gtaatggggt agctgtctcc aa 42

<210> SEQ ID NO 15
<211> LENGTH: 42
<212> TYPE: DNA
<213> ORGANISM: Artificial Sequence
<220> FEATURE:
<223> OTHER INFORMATION: Synthetic

<400> SEQUENCE: 15
cgggccctgc aggccctcga gcctagacac tttgataact ag 42

<210> SEQ ID NO 16
<211> LENGTH: 42
<212> TYPE: DNA
<213> ORGANISM: Artificial Sequence
<220> FEATURE:
<223> OTHER INFORMATION: Synthetic

<400> SEQUENCE: 16
agaattctta attaactcga gctagttatc aaagtgtcta gg 42

<210> SEQ ID NO 17
<211> LENGTH: 42
<212> TYPE: DNA
<213> ORGANISM: Artificial Sequence
<220> FEATURE:
<223> OTHER INFORMATION: Synthetic

<400> SEQUENCE: 17

-continued cgggccctgc aggccctcga ggatctatat ggtgaaaaat aa 42

<210> SEQ ID NO 18
<211> LENGTH: 42
<212> TYPE: DNA
<213> ORGANISM: Artificial Sequence
<220> FEATURE:
<223> OTHER INFORMATION: Synthetic

<400> SEQUENCE: 18
agaattctta attaactcga gttatttttc accatataga tc 42

<210> SEQ ID NO 19
<211> LENGTH: 42
<212> TYPE: DNA
<213> ORGANISM: Artificial Sequence
<220> FEATURE:
<223> OTHER INFORMATION: Synthetic

<400> SEQUENCE: 19
cgggccctgc aggccctcga gcctgaatat tctcttgaat aa 42

<210> SEQ ID NO 20
<211> LENGTH: 42
<212> TYPE: DNA
<213> ORGANISM: Artificial Sequence
<220> FEATURE:
<223> OTHER INFORMATION: Synthetic

<400> SEQUENCE: 20
agaattctta attaactcga gttattcaag agaatattca gg 42

<210> SEQ ID NO 21
<211> LENGTH: 45
<212> TYPE: DNA
<213> ORGANISM: Artificial Sequence
<220> FEATURE:
<223> OTHER INFORMATION: Synthetic

<400> SEQUENCE: 21
cgggccctgc aggccctcga gtggaatata tgggatggta aataa 45

<210> SEQ ID NO 22
<211> LENGTH: 42
<212> TYPE: DNA
<213> ORGANISM: Artificial Sequence
<220> FEATURE:
<223> OTHER INFORMATION: Synthetic

<400> SEQUENCE: 22
cgggccctgc aggccctcga gtctggaact ggtaaaattt aa 42

<210> SEQ ID NO 23
<211> LENGTH: 42
<212> TYPE: DNA
<213> ORGANISM: Artificial Sequence
<220> FEATURE:
<223> OTHER INFORMATION: Synthetic

<400> SEQUENCE: 23
agaattctta attaactcga gttaaatttt accagttcca ga 42

<210> SEQ ID NO 24
<211> LENGTH: 42
<212> TYPE: DNA
<213> ORGANISM: Artificial Sequence -continued
<220> FEATURE:
<223> OTHER INFORMATION: Synthetic

<400> SEQUENCE: 24
cgggccctgc aggccctcga gttctcgtac gcgttcctat aa 42

<210> SEQ ID NO 25
<211> LENGTH: 42
<212> TYPE: DNA
<213> ORGANISM: Artificial Sequence
<220> FEATURE:
<223> OTHER INFORMATION: Synthetic

<400> SEQUENCE: 25
agaattctta attaactcga gttataggaa cgcgtacgag aa 42

<210> SEQ ID NO 26
<211> LENGTH: 42
<212> TYPE: DNA
<213> ORGANISM: Artificial Sequence
<220> FEATURE:
<223> OTHER INFORMATION: Synthetic

<400> SEQUENCE: 26
cgggccctgc aggccctcga ggctaaatcc atacataact ga 42

<210> SEQ ID NO 27
<211> LENGTH: 42
<212> TYPE: DNA
<213> ORGANISM: Artificial Sequence
<220> FEATURE:
<223> OTHER INFORMATION: Synthetic

<400> SEQUENCE: 27
agaattctta attaactcga gtcagttatg tatggattta gc 42

<210> SEQ ID NO 28
<211> LENGTH: 42
<212> TYPE: DNA
<213> ORGANISM: Artificial Sequence
<220> FEATURE:
<223> OTHER INFORMATION: Synthetic

<400> SEQUENCE: 28
cgggccctgc aggccctcga ggattatgag tccatggatt aa 42

<210> SEQ ID NO 29
<211> LENGTH: 42
<212> TYPE: DNA
<213> ORGANISM: Artificial Sequence
<220> FEATURE:
<223> OTHER INFORMATION: Synthetic

<400> SEQUENCE: 29
agaattctta attaactcga gttaatccat ggactcataa tc 42

<210> SEQ ID NO 30
<211> LENGTH: 42
<212> TYPE: DNA
<213> ORGANISM: Artificial Sequence
<220> FEATURE:
<223> OTHER INFORMATION: Synthetic

<400> SEQUENCE: 30
cgggccctgc aggccctcga gcgtgatgat gtagatagat aa 42

<210> SEQ ID NO 31
<211> LENGTH: 42
<212> TYPE: DNA
<213> ORGANISM: Artificial Sequence
<220> FEATURE:
<223> OTHER INFORMATION: Synthetic

<400> SEQUENCE: 31
agaattctta attaactcga gttatctatc tacatcatca cg 42

<210> SEQ ID NO 32
<211> LENGTH: 42
<212> TYPE: DNA
<213> ORGANISM: Artificial Sequence
<220> FEATURE:
<223> OTHER INFORMATION: Synthetic

<400> SEQUENCE: 32
cgggccctgc aggccctcga ggtggaaact aagtatttct aa 42

<210> SEQ ID NO 33
<211> LENGTH: 42
<212> TYPE: DNA
<213> ORGANISM: Artificial Sequence
<220> FEATURE:
<223> OTHER INFORMATION: Synthetic

<400> SEQUENCE: 33
agaattctta attaactcga gttagaaata cttagtttcc ac 42

<210> SEQ ID NO 34
<211> LENGTH: 42
<212> TYPE: DNA
<213> ORGANISM: Artificial Sequence
<220> FEATURE:
<223> OTHER INFORMATION: Synthetic

<400> SEQUENCE: 34
cgggccctgc aggccctcga ggtattcgat gattattttt aa 42

<210> SEQ ID NO 35
<211> LENGTH: 42
<212> TYPE: DNA
<213> ORGANISM: Artificial Sequence
<220> FEATURE:
<223> OTHER INFORMATION: Synthetic

<400> SEQUENCE: 35
agaattctta attaactcga gttaaaaata atcatcgaat ac 42

<210> SEQ ID NO 36
<211> LENGTH: 42
<212> TYPE: DNA
<213> ORGANISM: Artificial Sequence
<220> FEATURE:
<223> OTHER INFORMATION: Synthetic

<400> SEQUENCE: 36
cgggccctgc aggccctcga gtggatcatg tgtgacatgt gt 42

<210> SEQ ID NO 37
<211> LENGTH: 42
<212> TYPE: DNA
<213> ORGANISM: Artificial Sequence
<220> FEATURE:
<223> OTHER INFORMATION: Synthetic -continued

<400> SEQUENCE: 37
agaattctta attaactcga gttactctct ataacaaata tc 42

<210> SEQ ID NO 38
<211> LENGTH: 45
<212> TYPE: DNA
<213> ORGANISM: Artificial Sequence
<220> FEATURE:
<223> OTHER INFORMATION: Synthetic

<400> SEQUENCE: 38
cgggccctgc aggccctcga ggtcaattgt gtaaagaaaa actaa 45

<210> SEQ ID NO 39
<211> LENGTH: 45
<212> TYPE: DNA
<213> ORGANISM: Artificial Sequence
<220> FEATURE:
<223> OTHER INFORMATION: Synthetic

<400> SEQUENCE: 39
agaattctta attaactcga gttagttttt ctttacacaa ttgac 45

<210> SEQ ID NO 40
<211> LENGTH: 42
<212> TYPE: DNA
<213> ORGANISM: Artificial Sequence
<220> FEATURE:
<223> OTHER INFORMATION: Synthetic

<400> SEQUENCE: 40
cgggccctgc aggccctcga ggaatctcct taatatgggt ac 42

<210> SEQ ID NO 41
<211> LENGTH: 42
<212> TYPE: DNA
<213> ORGANISM: Artificial Sequence
<220> FEATURE:
<223> OTHER INFORMATION: Synthetic

<400> SEQUENCE: 41
agaattctta attaactcga ggtacccata ttaaggagat tc 42

<210> SEQ ID NO 42
<211> LENGTH: 42
<212> TYPE: DNA
<213> ORGANISM: Artificial Sequence
<220> FEATURE:
<223> OTHER INFORMATION: Synthetic

<400> SEQUENCE: 42
cgggccctgc aggccctcga ggatgtgtag acatcaataa tt 42

<210> SEQ ID NO 43
<211> LENGTH: 42
<212> TYPE: DNA
<213> ORGANISM: Artificial Sequence
<220> FEATURE:
<223> OTHER INFORMATION: Synthetic

<400> SEQUENCE: 43
agaattctta attaactcga gaattattga tgtctacaca tc 42

RECOMBINANT VACCINIA VIRUS DERIVED FROM KVAC103 STRAIN

CROSS REFERENCE TO RELATED APPLICATION

This applications claims priority to Korean Patent Application No. 10-2014-140151, filed Oct. 16, 2014, the contents of such application being incorporated by reference herein.

FIELD OF THE INVENTION

The present invention relates to a novel recombinant virus derived from the attenuated vaccinia virus strain KVAC103.

DESCRIPTION OF THE PRIOR ART

Vaccinia virus is an enveloped DNA virus which has an about 120-180 kb double-stranded linear DNA genome encoding about 200 different genes (Hendrickson et al., 2010). Each of the genes is composed of a short 5'-promoter, a single ORF encoding a protein without intron, and a short 3'-polyadenylation site. These proteins are expressed in a promoter-dependent manner in the intermediate-early (IE), early (E) or late (L) stage of viral infection. The sequences of the early and late promoters have been well characterized through functional experiments (Rosel et al., 1986; Yuen et al., 1987; Davision et al., 1989a and 1989b; Chakrabarti et al., 1997).

Since vaccinia virus was first used as a vaccine for preventing smallpox by Edward Jenner in the 18th century, it has become a general term for immuomodulators such that it would give the etymology of the word “vaccine”. After the worldwide eradication of smallpox in 1977, vaccination of the population has not been done, but in recent years, the need for vaccination against smallpox bioterrorism has been proposed again. Vaccinia virus strains used in the early years had good immunogenic efficacy and greatly contributed to the eradication of smallpox, but people vaccinated with the vaccinia virus sometimes showed serious side effects such as systemic infection or progressive infection.

Virulence-attenuated vaccinia virus strains are developed to reduce such side effects including Modified vaccinia virus Ankara (MVA), NYVAC, and LC16m8. MVA is an attenuated virus strain obtained by subculturing the vaccinia virus CVA strain 500 times or more in chick embryo fibroblasts (CEFs), and it does not proliferate in most mammalian cells and has a 30 kb deletion region in six regions in the genome. This virus showed excellent safety in animal models, and thus have been developed as a smallpox vaccine and a vaccine delivery vehicle by Bavarian Nordic (Denmark). LC16m8, an attenuated virus strain developed by the Chiba Serum Institute of Japan, has characteristics in that it forms small plaques and shows reduced virulence. It was found to have a mutation in the B5R gene in the genome sequence. NYVAC is a virus strain obtained by deleting 18 ORFs from five regions in the genome of the Copenhagen strain by a genetic engineering technique, and has been developed as various recombinant viral delivery vehicles.

Viruses can be used as gene delivery vectors, because an exogenous genes can be inserted into the genome of viruses and overexpressed in the infected cells before delivery. In recent years, recombinant vaccinia viruses with an exogenous antigen inserted therein have been receiving highlights as vaccine delivery vectors.

In connection with this, Korean Patent No. 10-1241423 discloses the use of a virus as a gene delivery vector, and Korean Patent No. 10-1041691 discloses insertion of an exogenous DNA into the genome of the modified vaccinia virus (MVA) and the use of recombinant of MVA as vaccine.

SUMMARY OF THE INVENTION

An aspect of the present invention provides recombinant viruses comprising exogenous genes inserted into the genome of attenuated vaccinia virus strain KVAC103.

The present inventors have constructed a recombinant vaccinia virus strain by constructing a plasmid vector, which can comprise an exogenous gene, and inserting the constructed plasmid vector into the genome of the attenuated vaccinia virus strain KVAC103. In addition, the present inventors significantly enhanced the proliferation and replication of the recombinant virus by inserting and rescuing some of the KVAC103 genes, deleted during an attenuation process, into delivery vectors.

BRIEF DESCRIPTION OF THE DRAWINGS

The patent or application file contains at least one drawing executed in color. Copies of this patent or patent application publication with the color drawing(s) will be provided by the Office upon request and payment of the necessary fee.

FIG. 1 shows the entire sequence of pETL-EGFP.

FIG. 2 shows the structure of a pVVT1-EGFP shuttle plasmid vector.

FIG. 3 shows the PCR results of identifying KVAC103 by detecting a 19.5 kb deletion region and a 2.5 kb deletion region.

FIG. 4 shows ORFs present in the divided four domains (d1, d2, d3 and d4) from the 19.5 kb deletion region of KVAC103.

FIG. 5 shows the results of rescuing d1, d2, d3 and d4 regions from the 19.5 kb deletion region of KVAC103.

FIG. 6 shows the results of rescuing each of ORFs from the d1 and d3 regions.

FIG. 7 shows the nucleotide sequence of ORF5 and the amino acid sequence encoded by.

FIG. 8 shows the nucleotide sequence of ORF16 and the amino acid sequence encoded by.

FIG. 9 shows the spreading and replication of each recombinant virus strains in various mammalian host cell lines.

FIG. 10 shows the expression intensities of GFP in cells infected with each recombinant virus strain.

FIG. 11 shows the interferon sensitivities of recombinant vaccinia viruses.

FIG. 12 shows the skin toxicities of recombinant viruses in the rabbit skin.

FIG. 13 schematically shows steps of producing a recombinant KVAC103 virus for vaccine development by introducing an exogenous antigen gene (PA).

DETAILED DESCRIPTION OF THE INVENTION

Hereinafter, the present invention will be described in detail. However, the present invention can be embodied in different forms and is not limited to the embodiments described herein.

In one aspect, the present invention relates to a recombinant vaccinia virus derived from the attenuated vaccinia virus KVAC103 (accession No. KCCM11574P).

In an embodiment, the recombinant vaccinia virus may comprise a polynucleotide encoding an exogenous antigen, a polynucleotide represented by SEQ ID NO: 2, a polynucleotide represented by SEQ ID NO: 3, or a combination thereof. The polynucleotide of SEQ ID NO: 2 is the C7L gene of wild-type vaccinia virus, and the polynucleotide of SEQ ID NO: 3 is the K1L gene of wild-type vaccinia virus. In an example of the present invention, it was found that the attenuated vaccinia virus KVAC103 having the gene inserted therein had the effect of increasing the expression level of an exogenous antigen introduced in the virus. A variant of the gene sequence falls within the scope of the present invention, as long as it shows an increase in the expression level of the exogenous antigen. Specifically, the variant may comprise a nucleotide sequence having a sequence identity of at least 70%, preferably at least 80%, more preferably at least 90%, and most preferably at least 95%, to the nucleotide sequence of SEQ ID NO: 2 or 3. The "percentage (%) of sequence identity" for the polynucleotide is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences.

As used herein, the term "recombinant vaccinia virus" means a vaccinia virus containing one or more heterogeneous nucleotide, replicates heterogeneous nucleotide or expresses said nucleotide, a peptide, a heterogeneous peptide, or a protein encoded by a heterogeneous nucleotide in the virus infected cells. The recombinant virus can express a gene or a gene fragment in a sense or antisense form, which are not found in the natural state of the virus. In addition, the recombinant virus can express a gene which is found in a virus of a natural state. However, the gene is a modified gene, re-introduced or rescued into a gene of the virus by an artificial means. In an example of the present invention, the C7L or K11, gene, which is absent in the attenuated vaccinia virus KVAC103 but is present in wild-type vaccinia virus, re-introduced (rescued), and thus the proliferation of the virus and the expression of the exogenous gene increased.

In an embodiment, the recombinant vaccinia virus of the present invention comprises at least one marker gene or selection gene. The selection gene transduces a particular resistance to a cell, whereby a certain selection method becomes possible. The marker gene induces a color reaction in transduced cells, which can be used to identify transduced cells. For example, it may be the gene encoding β-galactosidase (β-gal), β-glucosidase (β-glu), green fluorescence protein (GFP), red fluorescence protein or blue fluorescence protein.

In an embodiment, the recombinant vaccinia virus of the present invention may comprise the plasmid vector of SEQ ID NO: 1.

In an embodiment, the plasmid vector may comprise a polynucleotide encoding an exogenous antigen, a polynucleotide represented by SEQ ID NO: 2, a polynucleotide represented by SEQ ID NO: 3, or a combination thereof.

In an embodiment, the plasmid vector may comprise an SfiI restriction site in the thymidine kinase (tk) gene of the vaccinia virus. In an example of the present invention, the exogenous gene in the recombinant virus was inserted into the thymidine kinase (tk) locus. However, the exogenous gene may be substituted or inserted into other loci to construct recombinant viruses, as long as it does not damage essential genes. For example, the exogenous gene may be inserted into a 19.5 kb deletion region or a 2.5 kb deletion region.

In an embodiment, the polynucleotide encoding the exogenous antigen is preferably either a gene encoding the antigen of viruses, bacteria or the like, which cause infectious diseases, or a portion of the gene.

The exogenous gene sequence encoding the exogenous antigen according to the present invention may also comprise two or more coding sequences linked to one or several transcription control elements. Preferably, the coding sequence encodes one or more proteins, polypeptides, peptides, exogenous antigens or antigenic epitopes, especially those described above with the therapeutically interesting genes. A heterologous or exogenous gene sequence is a sequence which is not normally found associated with the vaccinia virus as used in the present invention. The exogenous gene sequence may comprise two or more coding sequences.

In an embodiment, the polynucleotide encoding the exogenous antigen may be inserted into the SfiI restriction site.

In one aspect, the present invention relates to a vaccine composition containing the recombinant vaccinia virus of the present invention.

In an embodiment, the vaccine composition may contain the recombinant vaccinia virus expressing an exogenous antigen. The exogenous antigens may be disease-causing pathogenic genes, or genes encoding antigens derived from infectious microorganisms or homologous thereto. Thus, in the present invention, such therapeutically interesting genes can be presented to the immune system of an organism in order to affect, or more preferably to induce, a specific immune response and, thereby, vaccinate to protect the organism against an infection with the microorganism or virus. The therapeutically interesting genes are selected from genes of infectious viruses, for example, Dengue virus, Japanese encephalitis virus, Hepatitis virus B or C, or immunodeficiency viruses, such as HIV, but are not limited thereto.

For the preparation of vaccines, the recombinant vaccinia virus according to the invention is converted into a physiologically acceptable form. This can be done based on the experience in the preparation of poxvirus vaccines used for vaccination against smallpox (as described by Stickl, H. et al. Dtsch. med. Wschr. 99, 2386-2392 [1974]). For the preparation of vaccine shots, for example, virus particles are lyophilized in 100 ml of phosphate-buffered saline (PBS) in the presence of 2% peptone and 1% human albumin in an ampoule, preferably a glass ampoule. Alternatively, the vaccine shots are produced by stepwise freeze-drying of the virus in a formulation. This formulation can contain additional additives such as mannitol, dextran, sugar, glycine, lactose or polyvinylpyrrolidone or other aids, such as antioxidants or inert gas, stabilizers or recombinant proteins (for example, human serum albumin) suitable for in vivo administration. The glass ampoule is then sealed and can be stored between 4° C. and room temperature for several months. However, as long as no immediate need exists, the ampoule can preferably be stored at temperatures below −20° C. For vaccination or therapy, the lyophilisate of the composition can be dissolved in 0.1 to 0.5 ml of an aqueous solution, preferably physiological saline or Tris buffer, and administered either systemically or locally, i.e. parenterally, subcutaneously, intramuscularly, or any other administration routes known to those skilled in the art. The mode of administration, the dose and the number of administrations can be optimized by those skilled in the art in a known manner. However, most commonly, a patient is vaccinated with a second shot about one month to six weeks after the first vaccination shot.

In one aspect, the present invention relates to a pharmaceutical composition for immunotherapy containing the recombinant vaccinia virus.

In an embodiment of the present invention, the recombinant vaccinia virus of the present invention may also comprise, as an exogenous gene encoding an immunotherapy-related antigen, a disease-related gene having a therapeutic effect on proliferative diseases, cancer or metabolic diseases. For example, a therapeutically interesting gene regarding cancer could be a cancer antigen that has the capacity to induce a specific anti-cancer immune reaction.

In an embodiment of the present invention, the therapeutically effective dose of the pharmaceutical composition of the present invention can vary depending on various factors, for example, an administration method, a target area, the subject's conditions, etc. Thus, when the composition is to be used in the human body, the dose of the composition should be suitably determined by taking into consideration both safety and efficiency. It is also possible to estimate the dose for human administration from the effective dose determined through an animal test. Such considerations to be taken into the determination of the effective dose are described, for example, in Hardman and Limbird, eds., Goodman and Gilman's The Pharmacological Basis of Therapeutics, 10th ed. (2001), Pergamon Press; and E.W. Martin ed., Remington's Pharmaceutical Sciences, 18th ed. (1990), Mack Publishing Co.

The pharmaceutical composition of the present invention may also comprise a carrier, a diluent, an excipient, or a combination of two or more thereof, which are commonly used in biological formulations. The pharmaceutically acceptable carrier for use in the present invention is not specifically limited, as long as it is suitable for in vivo delivery of the composition. Examples of pharmaceutically acceptable carrier that may be used in the present invention include the compounds described in Merck Index, 13th ed., Merck & Co. Inc., physiological saline, sterile water, Ringer's solution, buffered saline, dextrose solution, maltodextrin solution, glycerol, ethanol, and mixtures containing one or more of these components. If necessary, the pharmaceutical composition may contain other conventional additives such as antioxidants, buffers, bacteriostatic agents and the like. In addition, the pharmaceutical composition can be prepared into injectable formulations, such as aqueous solutions, suspensions and emulsions, pills, capsules, granules or tablets, by adding diluents, dispersing agents, surfactants, binders and lubricants thereto. Furthermore, the pharmaceutical composition may preferably be formulated according to each disease or component by a suitable method known in the art or by using the method disclosed in Remington's Pharmaceutical Science (Mack Publishing Company, Easton Pa., 18th, 1990).

The pharmaceutical composition that is used in the present invention may further comprise pharmaceutically acceptable additives. Examples of pharmaceutically acceptable additives that may be used in the present, invention include starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, starch sodium glycolate, carnauba wax, synthetic aluminum silicate, stearic acid, magnesium stearate, aluminum stearate, calcium stearate, white sugar, dextrose, sorbitol, talc, etc. The pharmaceutically acceptable additives according to the present invention are preferably contained in an amount of 0.1-90 parts by weight based on the total weight of the composition, but are not limited thereto.

The composition of the present invention may be administered orally or parenterally (for example, intravenous, subcutaneous, intraperitoneal or topical application) according to the intended method. The dose of the composition of the present invention can vary depending on various factors, including the subject's weight, age, sex and health conditions, diet, administration time, administration method, excretion rate and the severity of the disease. The daily dose of the composition according to the present invention is 0.0001-10 mg/ml, preferably 0.0001-5 mg/ml, and is more preferably administered once or several times a day.

In one aspect, the present invention relates to a method for constructing a recombinant vaccinia virus, the method comprising inserting the plasmid vector of SEQ ID NO: 1 into the attenuated vaccinia virus KVAC103 by homologous recombination.

In an embodiment, the plasmid vector may comprise an SfiI restriction site in the thymidine kinase (tk) gene of the vaccinia virus.

In an embodiment, the plasmid vector may be inserted into the tk gene region of the attenuated vaccinia virus KVAC103. In an example of the present invention, an exogenous gene was inserted between two SfiI restriction sites in the tk gene of the plasmid vector, and then inserted into the tk gene of the attenuated vaccinia virus KVAC103 by homologous recombination.

In an embodiment, the plasmid vector may comprise a polynucleotide encoding an exogenous antigen, a polynucleotide represented by SEQ ID NO: 2, a polynucleotide represented by SEQ ID NO: 3, or a combination thereof.

In one aspect, the present invention relates to a method for constructing a recombinant attenuated vaccinia virus having an enhanced ability to replicate and proliferate, the method comprising the steps of:

a) infecting a cell with the above-described vaccinia virus KVAC103;

b) inserting a polynucleotide represented by SEQ ID NO: 2 or a polynucleotide represented by SEQ ID NO: 3 into a plasmid vector of SEQ ID NO: 1;

c) transfecting the plasmid vector of step b) into the cell of step a);

d) selecting a vaccinia virus having GFP inserted therein by homologous recombination. In an example of the present invention, it was shown that the attenuated vaccinia virus KVAC103 having the gene inserted therein had the effect of increasing the expression level of the exogenous antigen introduced in the virus.

In an embodiment, the polynucleotide of step b) may be inserted into cites other than between two SfiI restriction cites in the tk gene of the plasmid vector of SEQ ID NO: 1.

Hereinafter, the present invention will be described in further detail with reference to the following examples. It is to be understood, however, that these examples are for illustrative purposes only and are not intended to limit the scope of the present invention.

EXAMPLES

Example 1: Construction of Shuttle Plasmid (pVVT1-EGFP)

The genome DNA of the vaccinia virus strain KVAC103 (KCCM11574P) was purified. Using the purified genome as a template, PCR was performed using high-fidelity Phusion DNA polymerase (NEB), a TK-F primer (SEQ ID NO: 4) and a TK-R primer (SEQ ID NO: 5). The PCR product was electrophoresed on 1% agarose gel (low gelling temperature (LGT); Seaplaque Agarose; Cambrex #50100), and then separated, thereby producing a DNA fragment (1.7 kb) corresponding to the vaccinia virus thymidine kinase (J2R) gene and flanking sequence truncated at both ends. In addition, using a pBacPAK8 plasmid (Clontech) as a template, PCR was performed using a BP-F primer (SEQ ID NO: 6) and a BP-R primer (SEQ ID NO: 7). The PCR product was separated in the same manner as described above, thereby obtaining a 2.7 kb DNA fragment comprising an ampicillin-resistance gene and a replication origin of plasmid. The two DNA fragments were assembled using a Cold-fusion cloning kit (System Biosciences Inc.) according to the manufacturer's instruction, and the whole sequence of the plasmid was analyzed. The plasmid prepared as described above was named "pVVT0". 857-bp nucleotide (FIG. 1) comprising an early-to-late promoter (pETL) sequence (SEQ ID NO: 8) (Chakrabarti et al., 1997), a MCS (multiple cloning site) sequence (comprising ApaI, RsrII, SfiI, BamHI, XhoI and EcoRI restriction sites) and an EGFP (enhanced green fluorescent protein) sequence was synthesized by Bioneer (Korea), and then inserted into a pGEM-T easy vector The pETL-EGFP fragement from pGEM-T easy vector was subcloned into the ClaI/EcoRI restriction sites of the pVVT0 plasmid (see FIG. 1), thereby preparing the shuttle plasmid pVVT1-EGFP. The nucleotide sequence of the shuttle plasmid was analyzed and is shown in SEQ ID NO: 1 (see FIG. 2).

TABLE 1

| Primer name | Primer sequence (5'->3') | SEQ ID NO. |
|---|---|---|
| TK-F | GCC GAT TCA TTA AGC TTT TGC GAT CAA TAA ATG GA | 4 |
| TK-R | GGA GAA AAT ACC GGT ATA AAT ACT TAA TAA TCT C | 5 |
| BP-F | AGT ATT TAT ACC GGT ATT TTC TCC TTA CGC ATC T | 6 |
| BP-R | TAT TGA TCG CAA AAG CTT AAT GAA TCG GCC AAC G | 7 |
| pETL | TAA AAA TTG AAA TTT TAT TTT TTT TTT TTG GAA TAT AAA TAA | 8 |

Example 2: Construction of Recombinant Attenuated Vaccinia Virus Strain (KVAC103-GFP)

Optimization of KVAC103 Culture Conditions

The attenuated strain KVAC103 having a 19.57 kb [C9L-F3L] deletion region at the left and a 2.57 kb [A25L-A26L] deletion region at the right was used to construct a GFP-positive recombinant virus strain, but the virus did not proliferate. For this reason, the levels of proliferation of Vero cells (ATCC CCL781), infected with KVAC103, in various media and at various serum concentrations, were analyzed to determine the optimum culture conditions. Specifically, Vero cells were seeded in a 12-well plate, and then cultured with 1% FBS (Gibco #16000)-containing DMEM (Gendepot #CM0027050), Advanced-DMEM (Gibco #12491), OptiMEMI (Gibco #31985), VP-SFM (Gibco #11681) or OptiPro-SFM (Gibco #2309) medium for 24 hours. Then, the cells were infected with KVAC103 at a titer of 100 PFU/well for 2 hours. Thereafter, each of the media was replaced with the same medium containing 0%, 1%, 2% or 5% FBS, followed by culture for 3 days. The virus plaques were observed by staining with crystal violet solution. As a result, it was shown that the plaques were the clearest and largest in the OptiMEMI medium containing 1% FBS. Under such culture conditions, even a single virus plaque of KVAC103 could be amplified to generate large-scale virus stock. Thus, the above conditions are the optimum conditions for the replication of KVAC103 and the production of a recombinant virus.

Identification of KVAC103

Because the virus strain KVAC103 used for the production of a recombinant virus is difficult to culture, a method for examining identity of the viral stock is required. Thus, KVAC103 can be identified by amplifying the DNA sequence by PCR and sequencing the deletion region. The 19.5 kb deletion region of KVAC103 was amplified using a primer pair of 15F (SEQ ID NO: 9) and 35R (SEQ ID NO: 10), and the 2.5 kb deletion of KVAC103 was amplified using a primer pair of 140F (SEQ ID NO: 11) and 143R (SEQ ID NO: 12). The amplified PCR products were separated on agarose gel, and then sequenced, thereby identifying KVAC103 (FIG. 3). In addition, the wild-type vaccinia virus DNA was identified by PCR amplification using a primer pair of 15F (SEQ ID NO: 9) and 16R (SEQ ID NO: 13).

TABLE 2

| Region amplified | Primer name | Primer sequence (5'->3') | SEQ ID NO. |
|---|---|---|---|
| 19.5 kb deletion region | 15F | AGG AAC AGG ATC ATT GTC ATT ACA | 9 |
| T | 35R | TGA ACT AAA TGT TCC AGA GA GGA | 10 |
| 2.5 kb deletion region | 140F | AGT TCT GCA TTC AAT TCG GTG AGT | 11 |
| | 143R | AAT TGT ACC AAC GGT TCA AGA TGT | 12 |
| Wild-type vaccinia virus DNA | 15F | AGG AAC AGG ATC ATT GTC ATT ACA | 9 |
| | 16R | TCG TTT ATC AAC ACT ACC GTT AGA | 13 |

Construction of Recombinant KVAC-GFP

Because the proliferation of KVAC103 in Vero cells became possible under the optimized culture conditions, KVAC103 was used to construct a recombinant virus strain. Generally, there is no SfiI restriction site in the genomes of vaccinia virus Lister and other virus strains. Thus, a conventional homologous recombination method was slightly modified (Kan et al., 2012) in order to introduce two SfiI restriction sites (SfiI (A) and SfiI (B)) into the thymidine kinase locus of KVAC103 using the shuttle plasmid pVVT1-EGFP of Example 1, which has SfiI restriction sites. Specifically, Vero cells were infected with 0.01 MOI of KVAC103, and then transfected with the pVVT1-EGFP plasmid. Next, the cells were cultured in OptiMEMI medium containing 1% FBS for 6 days. Then, the Vero cells were re-infected with the diluted virus and covered with 1% agarose-containing medium. Plaque selection was performed in 3 cycles, and then the GFP-positive recombinant strain KVAC103 was obtained and named "KVAC-GFP virus". The Vero cells infected with KVAC103 showed delayed cell lysis or no cell lysis, and thus it was difficult to observe the viral infection of the cells. For this reason, the infection and propagation of the virus can be easily observed using the GFP-positive recombinant virus strains.

Example 3: Construction of Recombinant Attenuated Vaccinia Virus Strains by Rescuing Genes from the Deletion Region To find a gene minimally required for the replication of vaccinia virus was rescued from the 19.57 kb deletion region of KVAC103, which was expected to have a gene region associated with the replication of vaccinia virus. Specifically, the 19.57 kb deletion region of KVAC103 was divided into four domains (d1, d2, d3 and d4), each containing 5-7 ORFs and having a size of about 5 kb (FIG. 4). To amplify each domain by PCR, the genomic DNA purified from the Lister virus strain (Lancy-Vaxina smallpox vaccine, Berna Biotech, Switzerland, Lot. #15-501) was used as a template, and PCR was performed using the primer pairs shown in Table 3 below under the following conditions: 5 cycles, each consisting of 30 sec at 95° C., 30 sec at 45° C. and 6 min at 72° C.; and then 30 sec at 95° C., 30 sec at 55° C. and 6 min at 72° C. Each of the amplified DNA fragments was purified on agarose gel and subcloned into the XhoI restriction site of the pVVT1-EGFP plasmid (see FIG. 1) using an EZ-Cloning kit (Enzynomics, Korea). To avoid any mutation problem in the PCR process, high-fidelity Phusion DNA polymerase (NEB) was used, and two or more independently selected clones were used. 2 μg of each plasmid containing each of d1, d2, d3 and d4 was transfected into KVAC103-infected Vero cells with OptiMEMI for 4 hours using 2 μl of Lipofectamine2000. Then, the cells were cultured in 2% FBS-containing DMEM medium for 6 days. Six days after transfection, GFP-positive recombinant virus plaques were selected using the 5× fluorescence microscope IX71 (Olympus, Tokyo) and the digital imaging device DP72 (Olympus, Tokyo). The Vero cells were re-infected with the above selected virus stocks, and after 3 days of culture, the fluorescence image of the plaques was observed. The plaques were stained with crystal violet solution (0.15% crystal violet, 8% formaldehyde and 5% ethanol in distilled water) at room temperature for 5 minutes to observe the replication and proliferation of the recombinant virus. As a result, GFP-positive virus plaques were found in the wells transfected with the plasmids containing the d1 domain or the d3 domain. In addition, GFP-positive plaques were found in almost 100% of the re-infected cells.

TABLE 3

| Region amplified | Primer name | Primer sequence (5'->3') | SEQ ID NO. |
|---|---|---|---|
| d1 (4,496 bp) | C10L-15188F | AGAATTCTTAATTAACTCGAGTAATGGGG TAGCTGTCTCCAA | 14 |
| | C5L-19671R | CGGGCCCTGCAGGCCCTCGAGCCTAGACA CTTTGATAACTAG | 15 |
| d2 (4,819 bp) | C5L-19671F | AGAATTCTTAATTAACTCGAGCTAGTTAT CAAAGTGTCTAGG | 16 |
| | N1L-24489R | CGGGCCCTGCAGGCCCTCGAGGATCTATA TGGTGAAAAATAA | 17 |
| d3 (5,792 bp) | N1L-24489F | AGAATTCTTAATTAACTCGAGTTATTTTT CACCATATAGATC | 18 |
| | K4L-30282R | CGGGCCCTGCAGGCCCTCGAGCCTGAATA TTCTCTTGAATAA | 19 |
| d4 (3,881 bp) | K4L-30282F | AGAATTCTTAATTAACTCGAGTTATTCAA GAGAATATTCAGG | 20 |
| | F3L-34177R | CGGGCCCTGCAGGCCCTCGAGTGGAATATA TGGGATGGTAAATAA | 21 |

Thus, in order to construct a single ORF clone within the d1 domain and the d3 domain, PCR was performed using the primer pairs shown in Table 4 below under the same conditions as described above. Next, each of the PCR amplification products was subcloned into the Xho I restriction site of the pVVT1-EGFP plasmid.

TABLE 4

| Region amplified | Primer name | Primer sequence (5'->3') | SEQ ID NO. |
|---|---|---|---|
| ORF1 (319 bp) | C10L-15188F | AGAATTCTTAATTAACTCGAGTAATGGG GTAGCTGTCTCCAA | 14 |
| | 15338R | CGGGCCCTGCAGGCCCTCGAGTCTGGAA CTGGTAAAATTTAA | 22 |
| ORF2 (352 bp) | 15338F | AGAATTCTTAATTAACTCGAGTTATTTT TCACCAGTTCCAGA | 23 |
| | C9L-15690R | CGGGCCCTGCAGGCCCTCGAGTTCTCGT ACGCGTTCCTATAA | 24 |
| ORF3 (C9L, 1,947 bp) | C9L-15690F | AGAATTCTTAATTAACTCGAGTTATAGG AACGCGTACGAGAA | 25 |
| | C8L-17637R | CGGGCCCTGCAGGCCCTCGAGGCTAAAT CCATACATAACTGA | 26 |
| ORF4 (C8L, 605 bp) | C8L-17637F | AGAATTCTTAATTAACTCGAGTCAGTTA TGTATGGATTTAGC | 27 |
| | C7L-18242R | CGGGCCCTGCAGGCCCTCGAGGATTATG AGTCCATGGATTAA | 28 |
| ORF5 (C7L, 681 bp) | C7L-18242F | AGAATTCTTAATTAACTCGAGTTAATCC ATGGACTCATAATC | 29 |
| | C6L-18923R | CGGGCCCTGCAGGCCCTCGAGCGTGATG ATGTAGATAGATAA | 30 |
| ORF6 (C6L, 591 bp) | C6L-18923F | AGAATTCTTAATTAACTCGAGTTATCTA TCTACATCATCACG | 31 |
| | C5L-19671R | CGGGCCCTGCAGGCCCTCGAGCCTAGAC ACTTTGATAACTAG | 15 |
| ORF12 (N1L, 401 bp) | N1L-24489F | AGAATTCTTAATTAACTCGAGTTATTTT TCACCATATAGATC | 18 |
| | N2L-24890R | CGGGCCCTGCAGGCCCTCGAGGTGGAAA CTAAGTATTTCTAA | 32 |
| ORF13 (N2L, 486 bp) | N2L-24890F | AGAATTCTTAATTAACTCGAGTTAGAAA TACTTAGTTTCCAC | 33 |
| | M1L-26966R | CGGGCCCTGCAGGCCCTCGAGGTATTCG ATGATTATTTTTAA | 34 |
| ORF14 (M1L, 1,569 bp) | M1L-25376F | AGAATTCTTAATTAACTCGAGTTAAAAA TAATCATCGAATAC | 35 |
| | M2L-26945R | CGGGCCCTGCAGGCCCTCGAGTGGATCA TGTGTGACATGTGT | 36 |
| ORF15 (M2L, 797 bp) | M2L-26766F | AGAATTCTTAATTAACTCGAGTTACTCT CTATAACAAATATC | 37 |
| | K1L-27563F | CGGGCCCTGCAGGCCCTCGAGGTCAATT GTGTAAAGAAAAACTAA | 38 |
| ORF16 (K1L, 1,067 bp) | K1L-27563F | AGAATTCTTAATTAACTCGAGTTAGTTT TTCTTTACACAATTGAC | 39 |
| | K2L-28630R | CGGGCCCTGCAGGCCCTCGAGGAATCTC CTTAATATGGGTAC | 40 |
| ORF17 (K2L, 1,168 bp) | K2L-28630F | AGAATTCTTAATTAACTCGAGGTACCCA TATTAAGGAGATTC | 41 |
| | K3L-29798R | CGGGCCCTGCAGGCCCTCGAGGATGTGT AGACATCAATAATT | 42 |
| ORF18 (K3L, 484 bp) | K3L-29798F | AGAATTCTTAATTAACTCGAGAATTATT GATGTCTACACATC | 43 |
| | K4L-30282R | CGGGCCCTGCAGGCCCTCGAGCCTGAAT ATTCTCTTGAATAA | 19 |

As a result, it was shown that the clones obtained by rescuing ORF5 and ORF16 from the deletion region of KVAC103 produced a GFP-positive recombinant virus (FIG. 6). In addition, the whole sequence of the ORF5 and ORF16 clones was analyzed by sequencing. As a result, the nucleotide sequence encoding the 150 amino acids of ORF5 was exactly consistent with the C7L gene sequence (SEQ ID NO: 2) of the vaccinia virus (see FIG. 7), and the nucleotide sequence encoding the 284 amino acids of ORF16 was exactly consistent with the K1L gene sequence (SEQ ID NO: 3) (see FIG. 8). The C7L-rescued virus plaque was purified, and the purified plaque was named "KVAC-GFP-C7L virus". In addition, the K1L-rescued virus plaque was purified, and the purified plaque was named "KVAC-GFP-K1L virus".

Example 4: Construction of Recombinant Wild-Type Vaccinia Virus

Vero cells were seeded in a 12-well plate, and then infected with 0.02 MOI (multiplicity of infection) of a wild-type vaccinia virus Lister strain for 2 hours. After the medium was removed, 0.5 ml of serum-free OptiMEMI was added to the cells. The cells were transfected with 1.6 μg of pVVT1-EGFP and 4 μl of Lipofectamine2000 (Gibco) for 4 hours, and then the medium was replaced with 2% FBS-containing DMEM. Next, the cells were cultured for 5 days. The plaques grown on agarose overlayed medium were stained with 0.06% neutral red solution (in PBS) for 4 hours, and then selected with a wide bore tip (Molecular BioProduct #2069G), thereby obtaining GFP-positive recombinant viral plaques. As a result, a recombinant vaccinia virus derived from the Lister strain was constructed and named "Lister-GFP" virus.

EXPERIMENTAL EXAMPLES

Experimental Example 1: Measurement of Titers of Recombinant Viruses and Determination of Host Range of the Viruses In order to measure the titers of the recombinant vaccinia viruses (KVAC-GFP, KVAC-GFP-C7L, KVAC-GFP-K1L and Lister-GFP), Vero cells were adapted in 2% FBS-containing OptiMEMI (Gibco), and then 1 ml of 2% FBS-containing OptiMEMI containing Vero cells at a density of $4\times10^5$ cells/ml was seeded into each well of a 12-well plate. 16-26 hours after seeding, the cells were infected with 100 μl of each of 10-fold dilutions of the recombinant virus strains for 2 hours. The medium was replaced with 1% FBS-containing OptiMEMI, and the cells were cultured for 3 days. The viral plaques were stained with crystal violet dye solution at room temperature for 5 minutes to measure the titers. In addition, because the C7L and K1L genes are known as host range genes, the proliferation and replication of the rescued recombinant viruses were examined in various mammalian cell lines. In order to determine the host ranges of the recombinant vaccinia virus strains (KVAC-GFP, KVAC-GFP-C7L, KVAC-GFP-K1L and Lister-GFP), the virus strains were infected into the mammalian cell lines 143B (ATCC CRL-8303), Vero, BSC-40 (ATCC CRL-2761), MA-104 (ATCC CRL-2378) and RK-13 (ATCC CCL-37). Specifically, each of 143B, Vero, BSC-40, MA-104 and RK-13 was seeded in a 12-well plate, and then infected with 0.01 MOI of KVAC-GFP, KVAC-GFP-C7L, KVAC-GFP-K1L or Lister-GFP. 48 hours after infection, the size of the GFP-positive plaques was measured with the 5× inverted fluorescence microscope IX72. The titers of the viruses were measured 3 days post-infection (DPI) by counting viral plaques, which were cultured in the Vero cells and stained, and the replication of the viruses was measured by the fold increase in the titer of virus. FIG. 9 shows the results of analyzing the virus spreading proliferation in the virus-infected Vero, BSC-40, MA-104 and RK-13 cells by GFP fluorescence, and Table 5 below shows the results of analyzing the replication of the viruses. It could be seen that KVAC-GFP could proliferate only in Vero cells at low serum concentrations and in MA-104. However, the C7L-rescued virus and the K1L-rescued virus could also replicate in four of the five cell lines. Thus, it could be seen that the host range of the C7L gene- or K1L gene-rescued virus was expanded.

TABLE 5

| Cells | ATCC # | Species | Tissue | KVAC-GFP | C7L-GFP | K1L-GFP | Lister-GFP |
|---|---|---|---|---|---|---|---|
| 143B | CRL-8303 | Human | Osteo-carcinoma | − | ++ | ++ | ++ |
| Vero | CCL-81 | Green Monkey | Kidney | −/++ | ++ | ++ | ++ |
| BSC 40 | CRL-2761 | Green Monkey | Kidney | − | ++ | ++ | ++ |
| MA-104 | CRL-2378 | Rhesus Monkey | Kidney | ++ | ++ | ++ | ++ |
| RK-13 | CCL-37 | Rabbit | Kidney | − | − | − | ++ |

Experimental Example 2: Measurement of Proliferation of Recombinant Viruses

The GFP expression levels of the recombinant virus strains (KVAC-GFP, KVAC-GFP-C7L, KVAC-GFP-K1L and Lister-GFP) were compared. Specifically, Vero cells were seeded in 1% FBS-containing OptiMEMI medium, and then infected with 0.1 MOI of each of the recombinant virus strains and cultured for 3 days. The fluorescence intensity of the cells was measured with the multi-well plate reader SpectraMax M5 (Molecular Device) (excitation wavelength: 480 nm, emission wavelength: 509 nm, and cutoff wavelength: 495 nm). As a result, it was shown that the GFP expression level of the C7L- or K1L-rescued virus was higher than that of KVAC-GFP. Particularly, the GFP intensity of the C7L-rescued virus (KVAC-GFP-C7L) was about 10 times higher than that of KVAC-GFP (FIG. 10). Such results are very important in the development of recombinant vaccines. This is because if antigen genes are inserted into the GFP gene locus, the expression level thereof will increase about 10 times compared to those of conventional antigens to induce a very strong immune response.

Experimental Example 3: Interferon Sensitivities of C7L- and K1L-Rescued Viruses It is known that C7L and K1L function as interferon antagonists (Gillard et al., 1985 and 1986; Perkus et al., 1989 and 1990; Meng et al., 2009 and 2012; reviewed by Werden et al., 2008). Thus, the functional effects of C7L and K1L were analyzed by examining the interferon sensitivities of the KVAC103-derived recombinant viruses (KVAC-GFP, KVAC-GFP-C7L and KVAC-GFP-K1L) and Lister-GFP. Specifically, Vero cells were infected with 0.005 MOI of each of the recombinant viruses, and the medium was replaced with medium containing 0, 20, 200 or 2000 units/ml of interferon-beta 1a (INF1a) (Gibco #PHC4244). The proliferation of the viruses was observed using a GFP expression marker. As a result, it was shown that the four recombinant virus strains had different interferon sensitivities (FIG. 11). It could be seen that the replication of KVAC-GFP was completely inhibited by the lowest concentration of interferon, indicating that KVAC-GFP is most sensitive to interferon. In addition, the C7L- or K1L-rescued virus strain showed interferon sensitivity lower than KVAC103, suggesting that it acquired an interferon-resistance phenotype due to rescue of the C7L or K1L gene. Thus, the interferon sensitivity was lower in the order of KVAC-GFP<KVAC-GFP-C7L, KVAC-GFP-K1L<Lister-GFP.

Experimental Example 4: Animal Skin Toxicity Test

Using 8-week-old female New Zealand white rabbits (weight: about 2 kg), the skin toxicity of the recombinant viruses was examined. Specifically, the rabbit skin was shaved, and then infected with 30 ul (1×106 PFU/ml) of each of KVAC-GFP, KVAC-GFP-C7L and KVAC-GFP-K1L viruses by scarification. The infected skin area was observed daily for 2 weeks, and the severity and the size of the infected area were recorded. As a result, it was shown that the area infected with Lister-GFP virus was the severest and most chronic, and the next was KVAC-GFP-K1L virus. The area infected with KVAC-GFP-C7L or KVAC-GFP virus was the slightest and was recovered most rapidly. Thus, it could be seen that the recombinant vaccinia virus strains obtained by rescuing C7L or K1L from the KVAC103 strain were less toxic than the conventional Lister virus (FIG. 12).

Experimental Example 5: Development of Vaccine Using Recombinant Attenuated Vaccinia Virus In order to develop a vaccine using the recombinant attenuated vaccinia virus of the present invention, a recombinant vaccinia virus was produced according to the process shown in FIG. 13, and the immunogenic effect thereof was tested. Specifically, a desired antigen gene was inserted into the pVVT1-EGFP-C7L vector using the SfiI restriction enzyme, and then transfected into KVAC103-infected Vero cells. Thereafter, the cells were cultured in 5% serum-containing medium, and then the immunogenic effect of the virus in mice was examined.

The attenuated virus strain KVAC103 had a disadvantage over the wild-type vaccinia strain Lister in that it is difficult to proliferate and replicate. However, the recombinant attenuated virus strain obtained by rescuing the C7L or K1L gene among the deleted genes had an enhanced ability to proliferate and replicate in various hosts, and the toxicity thereof was similar to that of the original attenuated strain KVAC103. Thus, the recombinant virus strains of the present invention can be used as viral vectors for expressing and delivering an exogenous antigen. Furthermore, these recombinant virus strains are less toxic, and thus can be used as vaccines for infectious diseases by introducing the antigens of other infectious disease-causing strains or viruses. In addition, these recombinant virus strains can be used as immunotherapeutic vaccines that express an exogenous gene encoding an immunotherapy-related antigen.

As described above, the recombinant vaccinia virus of the present invention is derived from the attenuated vaccinia virus strain KVAC103, and can express an exogenous gene in a host while causing little or no toxicity when cells are infected with the recombinant vaccinia virus. In addition, the recombinant vaccinia virus has an expanded host range and an enhanced ability to replicate and proliferate, and thus can significantly express an exogenous gene in a host. Therefore, it is expected that the recombinant vaccinia virus can be effectively used as a vaccine composition having an excellent immunogenic effect or a virus vector having an excellent gene delivery effect.

Accession Number

Depository authority: Korean Culture Center of Microorganisms;

Accession number: KCCM11574P;

Deposit date: Oct. 1, 2014.

What is claimed is:

1. A recombinant vaccinia virus comprising a heterologous polynucleotide inserted into a thymidine kinase (tk) gene locus of a genome of attenuated vaccinia virus KVAC103 (accession No. KCCM11574P), wherein the heterologous polynucleotide encodes at least one protein.

2. The recombinant vaccinia virus of claim 1, wherein the heterologous polynucleotide comprises a polynucleotide encoding a fluorescent protein, a polynucleotide encoding an antigen, a polynucleotide represented by SEQ ID NO: 2, a polynucleotide represented by SEQ ID NO: 3, or a combination thereof.

3. A vaccine composition containing the recombinant vaccinia virus of claim 2.

4. A vaccine composition containing the recombinant vaccinia virus of claim 1.

5. A method for constructing a recombinant vaccinia virus comprising a heterologous polynucleotide, the method comprising the steps of:

A) Inserting the heterologous polynucleotide into a restriction site of a plasmid vector for producing a recombinant vaccinia virus; and B) inserting the heterologous polynucleotide, inserted into the plasmid vector in step A, into the thymidine kinase gene locus of a genome of attenuated vaccinia virus KVAC103 by homologous recombination;

wherein the heterologous polynucleotide encodes at least one protein, and wherein the heterologous polynucleotide comprises a polynucleotide encoding a fluorescent protein, a polynucleotide encoding an antigen, a polynucleotide represented by SEQ ID NO: 2, a polynucleotide represented by SEQ ID NO: 3, or a combination thereof.

6. The method of claim 5, wherein the plasmid vector is represented by SEQ ID NO: 1.

7. The method of claim 5, wherein the plasmid vector comprises:

A thymidine kinase (tk) gene locus sequence of attenuated vaccinia virus KVAC103 (accession No. KCCM11574P), an ampicillin resistance gene, a replication origin, an early-to-late promoter, a multicloning site (MCS) sequence, and a polynucleotide encoding an enhanced green fluorescent protein (EGFP).

* * * * *